(12) United States Patent
Ortiz et al.

(10) Patent No.: US 8,252,006 B2
(45) Date of Patent: Aug. 28, 2012

(54) SINGLE PASS GASTRIC RESTRICTION WITH A CORKSCREW STYLE WALL ANCHOR

(75) Inventors: Mark S. Ortiz, Milford, OH (US); David B. Griffith, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 845 days.

(21) Appl. No.: 11/197,544

(22) Filed: Aug. 5, 2005

(65) Prior Publication Data

US 2007/0032797 A1 Feb. 8, 2007

(51) Int. Cl.
*A61B 17/10* (2006.01)
(52) U.S. Cl. ...................................................... 606/142
(58) Field of Classification Search .................. 606/142, 606/153, 139, 143, 213–221
See application file for complete search history.

(56) References Cited

U.S. PATENT DOCUMENTS

| | | | |
|---|---|---|---|
| 5,080,663 A | 1/1992 | Mills et al. | |
| 5,376,101 A | 12/1994 | Green et al. | |
| 5,437,681 A | 8/1995 | Meade et al. | |
| 5,462,558 A | 10/1995 | Kolesa et al. | |
| 5,514,159 A | 5/1996 | Matula et al. | |
| 5,520,700 A * | 5/1996 | Beyar et al. | 606/139 |
| 5,540,705 A | 7/1996 | Meade et al. | |
| 5,571,119 A | 11/1996 | Atala | |
| 5,582,616 A * | 12/1996 | Bolduc et al. | 606/143 |
| 5,709,693 A | 1/1998 | Taylor | |
| 5,713,910 A | 2/1998 | Gordon et al. | |
| 5,814,071 A | 9/1998 | McDevitt et al. | |
| 5,830,221 A * | 11/1998 | Stein et al. | 606/157 |
| 6,036,694 A | 3/2000 | Goble et al. | |
| 6,346,111 B1 | 2/2002 | Gordon et al. | |
| 6,443,962 B1 | 9/2002 | Gaber | |
| 6,454,778 B2 | 9/2002 | Kortenbach | |
| 6,494,888 B1 | 12/2002 | Laufer et al. | |
| 6,506,196 B1 | 1/2003 | Laufer | |
| 6,558,400 B2 * | 5/2003 | Deem et al. | 606/151 |
| 6,656,194 B1 | 12/2003 | Gonnoe et al. | |
| 6,663,633 B1 * | 12/2003 | Pierson, III | 606/72 |
| 6,663,639 B1 | 12/2003 | Laufer et al. | |
| 6,669,714 B2 * | 12/2003 | Coleman et al. | 606/219 |
| 6,719,763 B2 | 4/2004 | Chung et al. | |
| 6,719,764 B2 | 4/2004 | Gellman et al. | |
| 6,746,460 B2 | 6/2004 | Gannoe et al. | |
| 6,755,843 B2 | 6/2004 | Chung et al. | |
| 6,773,440 B2 | 8/2004 | Gannoe et al. | |
| 6,835,200 B2 | 12/2004 | Laufer et al. | |
| 6,908,427 B2 | 6/2005 | Fleener et al. | |
| 6,923,819 B2 | 8/2005 | Meade et al. | |

(Continued)

FOREIGN PATENT DOCUMENTS

EP 1545336 6/2005

(Continued)

*Primary Examiner* — Gary Jackson
*Assistant Examiner* — Lindsey Bachman

(57) ABSTRACT

A gastric reduction apparatus endoscopically draws stomach walls into apposition. The apparatus includes an applicator body having a proximal end and a distal end. The applicator body also includes a suction slot shaped and dimensioned for housing a corkscrew anchor. A firing mechanism is associated with the corkscrew anchor for rotation of the corkscrew anchor in a manner causing the corkscrew anchor to penetrate and engage tissue brought adjacent the suction slot. A method for gastric reduction is achieved by introducing a gastric reduction apparatus as disclosed above within the stomach of an individual, applying the corkscrew anchor to a stomach wall and drawing stomach walls together to create a cavity within the stomach.

5 Claims, 4 Drawing Sheets

U.S. PATENT DOCUMENTS

| | | |
|---|---|---|
| 6,945,980 B2 * | 9/2005 | Nguyen et al. .............. 606/151 |
| 7,087,064 B1 * | 8/2006 | Hyde ........................ 606/142 |
| 2001/0023352 A1 | 9/2001 | Gordon et al. |
| 2002/0107530 A1 | 8/2002 | Sauer et al. |
| 2002/0183768 A1 | 12/2002 | Deem et al. |
| 2003/0065359 A1 * | 4/2003 | Weller et al. ............... 606/213 |
| 2003/0083674 A1 | 5/2003 | Gibbens, III |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0172047 A1 | 9/2004 | Gellman et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |

FOREIGN PATENT DOCUMENTS

| | | |
|---|---|---|
| EP | 1569709 | 9/2005 |
| WO | WO0061012 | 10/2000 |
| WO | WO01/10312 | 2/2001 |
| WO | WO0166001 | 9/2001 |
| WO | WO0189393 | 11/2001 |
| WO | WO02/35980 | 5/2002 |

* cited by examiner

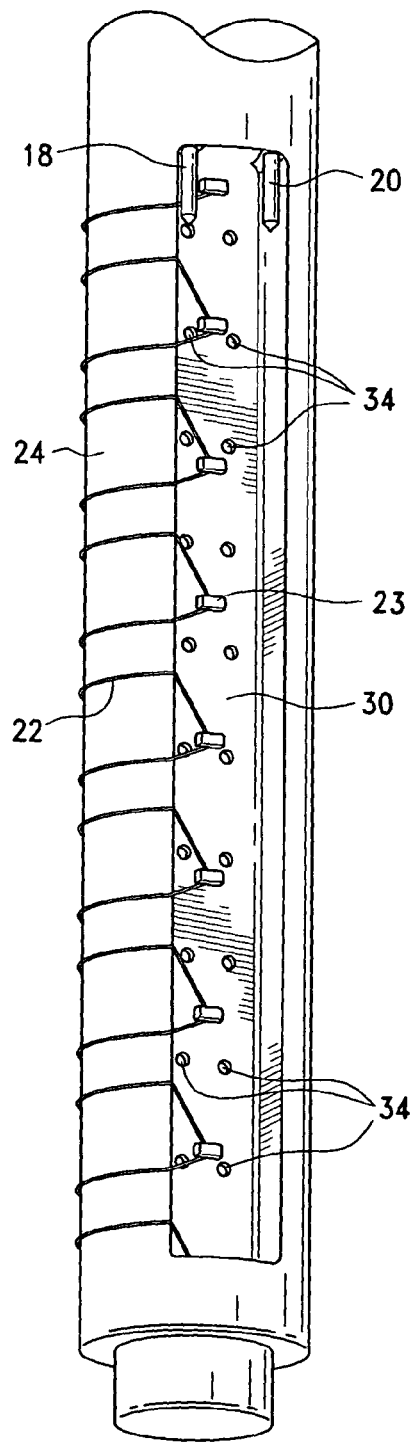
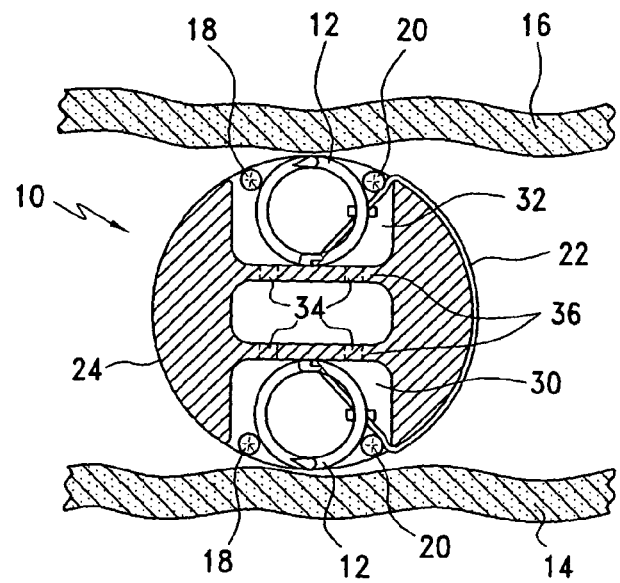
FIG. 6
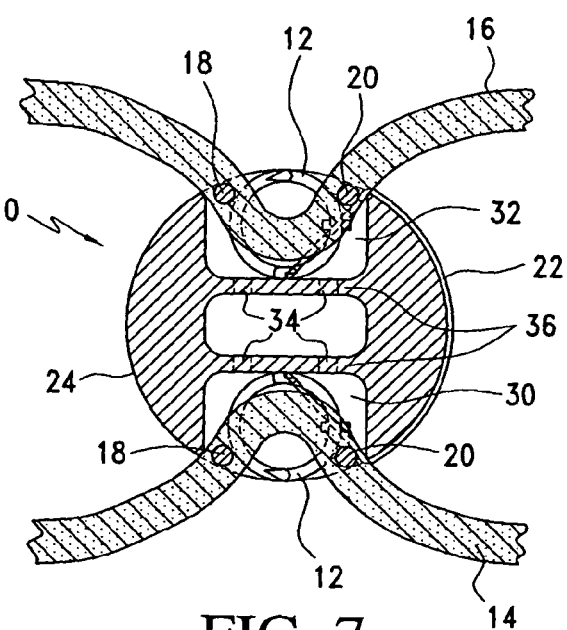
FIG. 7
FIG. 5

SINGLE PASS GASTRIC RESTRICTION WITH A CORKSCREW STYLE WALL ANCHOR

BACKGROUND OF THE INVENTION

1. Field of the Invention

The present invention relates to gastric reduction surgery. More particularly, the invention relates to a method and apparatus for performing gastric reduction surgery endoscopically through the implementation of a corkscrew style wall anchor.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. One of the most commonly performed procedures is Roux-en-Y gastric bypass (RYGB). This procedure is highly complex and is utilized to treat people exhibiting morbid obesity. Even though this is a complex operation, greater than 100,000 procedures are performed annually in the United States alone. Other forms of bariatric surgery include Fobi pouch, bilio-pancreatic diversion, and gastroplastic or "stomach stapling". In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secret stomach juices flowing through the intestinal track.

A segment of the small intestine is then brought from the lower abdomen and joined with the upper pouch to form an anastomosis created through a half-inch opening, also called the stoma. This segment of the small intestine is called the "Roux loop" and carries the food from the upper pouch to the remainder of the intestines, where the food is digested. The remaining lower pouch, and the attached segment of duodenum, are then reconnected to form another anastomotic connection to the Roux loop at a location approximately 50 to 150 cm from the stoma, typically using a stapling instrument. It is at this connection that the digestive juices from the bypass stomach, pancreas, and liver, enter the jejunum and ileum to aid in the digestion of food. Due to the small size of the upper pouch, patients are forced to eat at a slower rate and are satiated much more quickly. This results in a reduction in caloric intake.

The conventional RYGB procedure requires a great deal of operative time. Because of the degree of invasiveness, post-operative recovery time can be quite lengthy and painful.

In view of the highly invasive nature of the current RYGB procedure, other less invasive procedures have been developed. The most common form of gastric reduction surgery involves the application of vertical staples along the stomach to create an appropriate pouch. This procedure is commonly performed laparoscopically and, as such, requires substantial preoperative, operative, postoperative resources.

With the foregoing in mind, procedures that allow for the performance of gastric reduction surgery in a time efficient and patient friendly manner are needed. The present invention provides such a method and an associated apparatus.

SUMMARY OF THE INVENTION

It is, therefore, an object of the present invention to provide a gastric reduction apparatus for endoscopically drawing stomach walls into apposition. The apparatus includes an applicator body including a proximal end and a distal end. The applicator body also includes a suction slot shaped and dimensioned for housing a corkscrew anchor. A firing mechanism is associated with the corkscrew anchor for rotation of the corkscrew anchor in a manner causing the corkscrew anchor to penetrate and engage tissue brought adjacent the suction slot.

It is also an object of the present invention to provide a method for gastric reduction. The method is achieved by introducing a gastric reduction apparatus as disclosed above within the stomach of an individual, applying the corkscrew anchor to a stomach wall and drawing stomach walls together to create a cavity within the stomach.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 4 and 5 are detailed view of the applicator body of the gastric reduction apparatus with and without the corkscrew anchor positioned therein, respectively.

FIGS. 6, 7, 8 and 9 are cross sectional views showing operation of the gastric reduction apparatus.

DESCRIPTION OF THE PREFERRED EMBODIMENT

Figure 1:
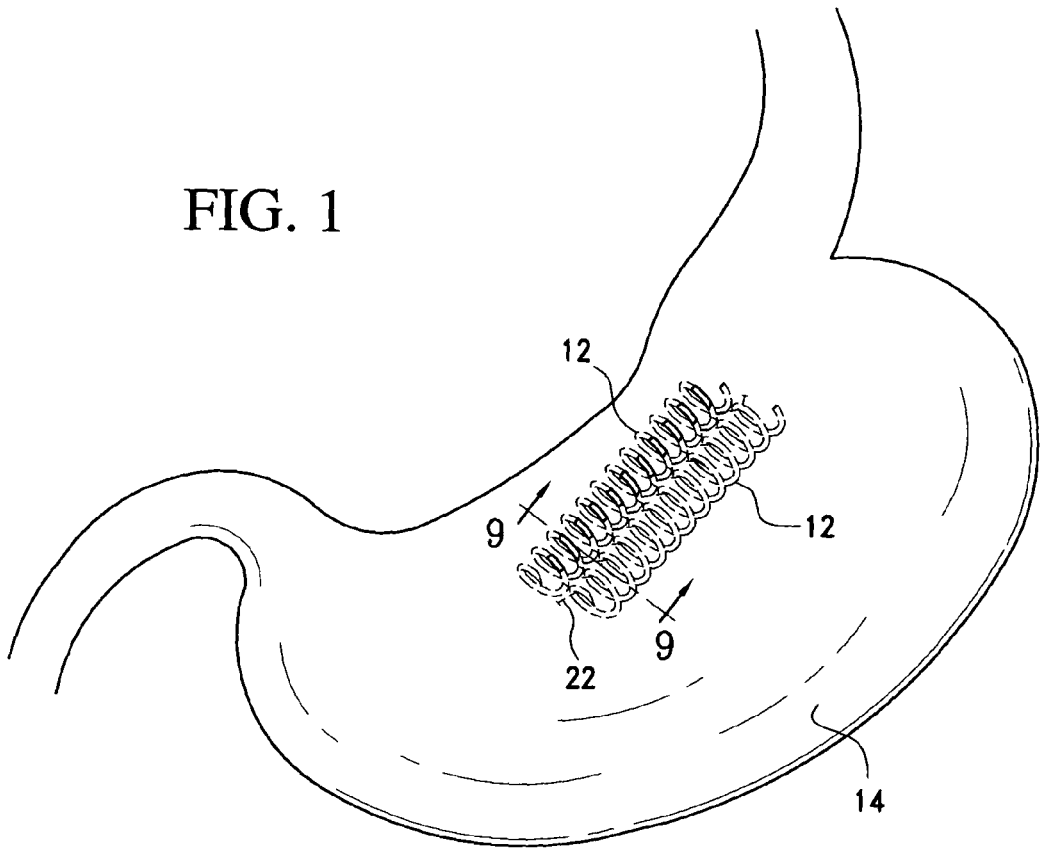
FIG. 1 is a perspective view of the corkscrew anchors of the present invention used in gastric reduction surgery.
Figure 2:
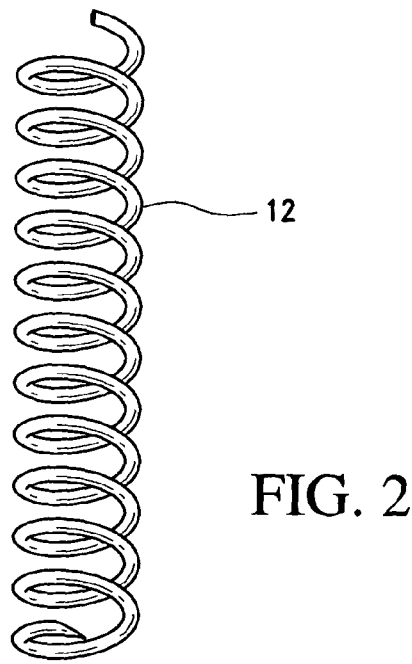
FIG. 2 is a perspective view of a corkscrew anchor in accordance with the present invention.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

Referring to the various figures, an endoscopic gastric reduction apparatus 10 for efficiently performing gastric reduction surgery is disclosed. The gastric reduction apparatus 10 functions by applying respective corkscrew anchors 12 to anterior and posterior gastric walls 14, 16 for the creation of a closure generated by pulling the anterior and posterior walls 14, 16 together.

In general, the gastric reduction apparatus 10 uses suction to respectively draw the anterior and posterior stomach walls 14, 16 into contact with the gastric reduction apparatus 10.

Thereafter, retention bars 18, 20 are advanced across the access openings of the gastric reduction apparatus 10 and through the tissue held therein to securely hold the anterior and posterior stomach walls 14, 16 adjacent the apparatus 10. The stomach tissue is held in a configuration in which the gaps in the gastric reduction apparatus 10 are spaced at the same pitch as the corkscrew anchors 12 and the gaps will allow for a full thickness tissue penetration.

In particular, the corkscrew anchors 12 pass alternately through mucosa, muscular layer and serosa, and then back through the stomach wall in a reverse, rotational direction. This results in full thickness penetration of the stomach wall. The tight hold of the suction on the tissue ensures that the corkscrew anchors 12 never touch adjacent organs. The vacuum is then replaced with light insufflation to remove the anterior and posterior stomach walls 14, 16 from the gastric reduction apparatus 10.

Once the corkscrew anchors 12 are installed, the gastric reduction apparatus 10 is extracted to allow the cinching of a pre-woven suture 22 passing through the corkscrew anchors 12 to form the gastric pouch. In particular, this results in the application of two opposing corkscrew anchors 12 that are subsequently pulled together through the utilization of a pre-woven mattress stitch suture 22 cinched down over the two corkscrew anchors 12. Although a mattress stitch is disclosed in accordance with a preferred embodiment of the present invention, those skilled in the art will appreciate other stitch patterns may be used without departing from the spirit of the present invention.

Figure 3:
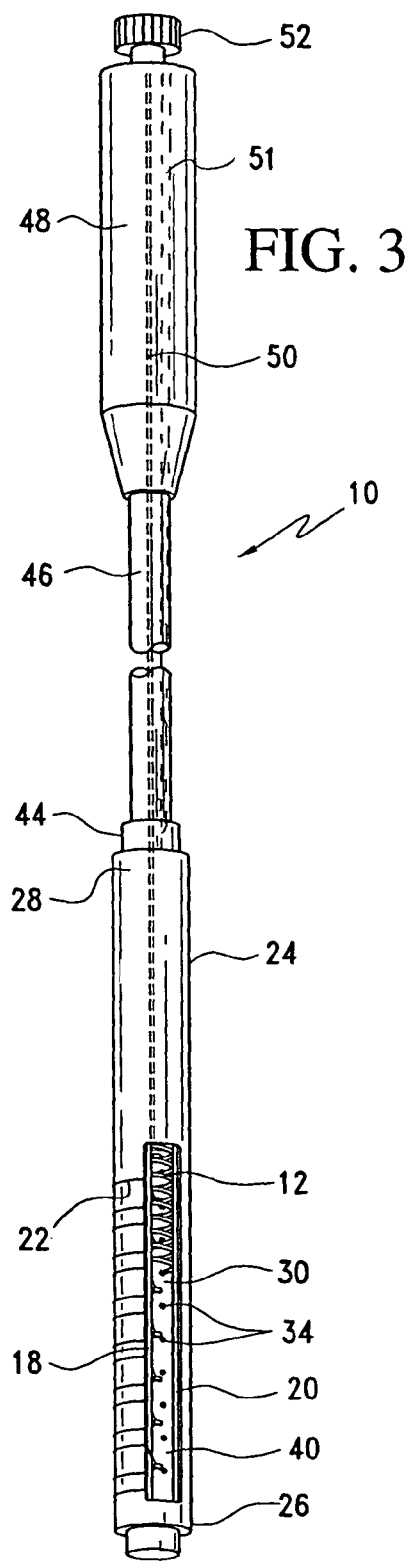
FIG. 3 is a side view of the present gastric reduction apparatus.
Figure 4:
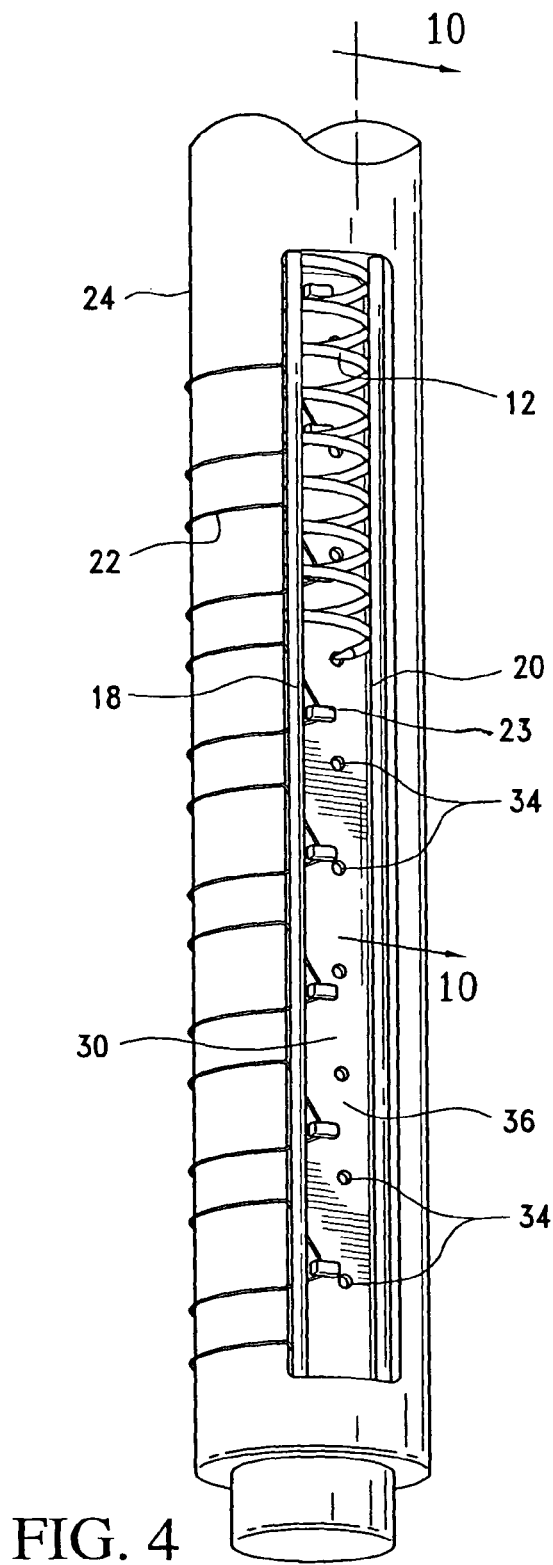
Figure 8:
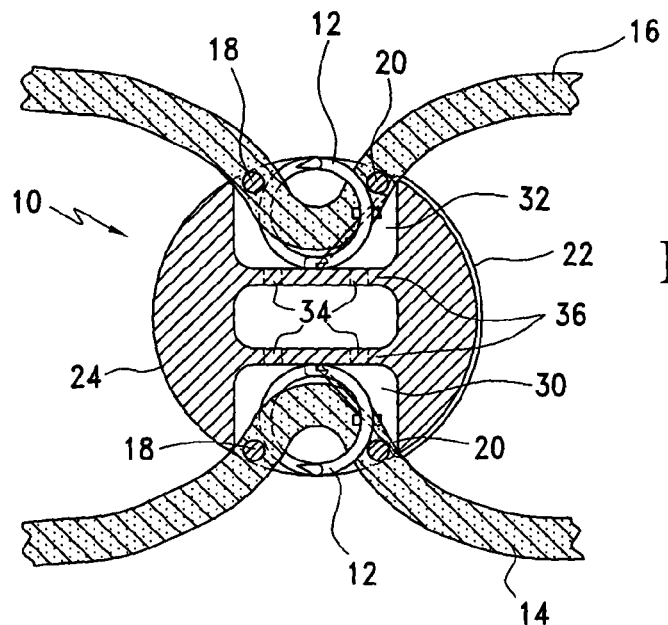
Figure 9:
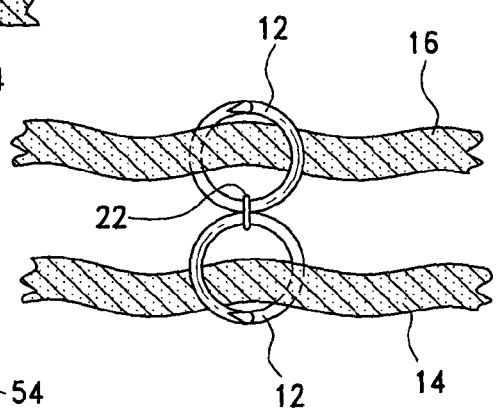
Figure 10:
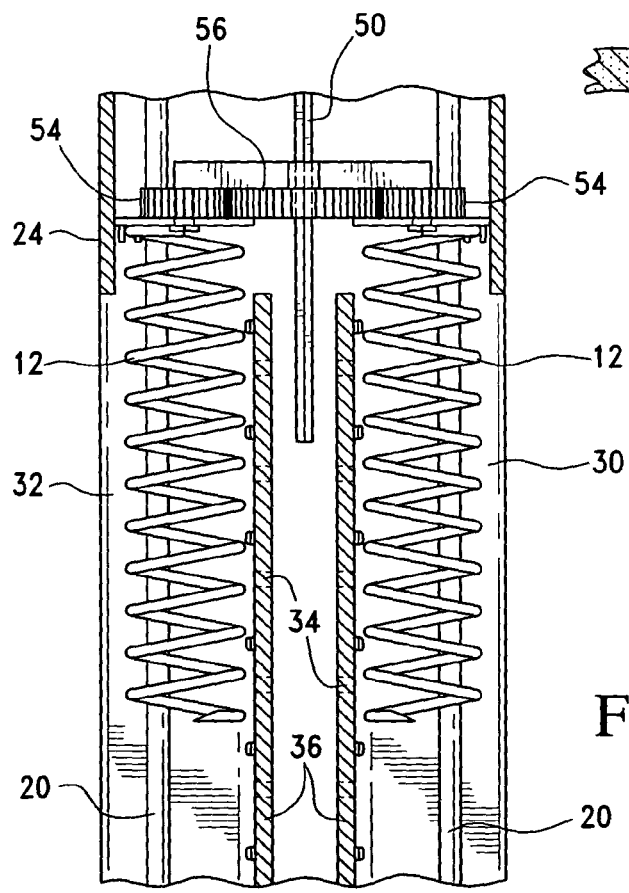
FIG. 10 is a detailed interior view of the gastric reduction apparatus.

With reference to FIGS. 3 through 10, the gastric reduction apparatus 10 includes a longitudinally extending applicator body 24 having a distal end 26 and a proximal end 28. The applicator body 24 has anterior and posterior suction slots 30, 32 shaped and dimensioned for housing respective corkscrew anchors 12. The suture 22 is pre-woven for access to the suction slots 30, 32 and the corkscrew anchors 12 respectively held therein. The suture 22 is held in position within the suction slots 30, 32 by retaining member 23 about which the suture 22 is threaded in a predetermined manner alternately attaching the anterior and posterior sides allowing for attachment to the corkscrew anchors 12 and release from the applicator body 24 once the anchor members 12 are secured to the stomach wall. Since the anterior and posterior sides of the applicator body 24 are substantially identical, only the anterior suction side will be described in detail.

The anterior suction slot 30 includes a series of suction holes 34 formed within the central wall 36 of the applicator body 24. The central wall 36 divides the anterior suction slot 30 from the posterior suction slot 32 and is substantially hollow for the creation of a vacuum in accordance with the present invention. The anterior suction slot 30 is shaped and dimensioned for receiving tissue therein. The anterior suction slot 30 extends along the applicator body 24 defining a recess 36 into which the anterior stomach tissue may be respectively drawn during the installation of the corkscrew anchor 12.

The applicator body 24 also includes a storage section 40 adjacent the anterior suction slot 30 in which the corkscrew anchor 12 is stored prior to the installation in accordance with the present invention. The storage section 40 is partially covered and sits directly adjacent the anterior suction slot 30. In this way, and as will be discussed below in greater detail, the corkscrew anchor 12 will move distally within the applicator body 24 as the corkscrew anchor 12 is rotated and threaded upon the tissue of the stomach wall 14, 16.

With regard to the corkscrew anchor 12, it is formed in the shape of a spiral and includes a pointed first end shaped and dimensioned for penetration through the stomach tissue in the manner discussed below. The corkscrew anchor is preferably manufactured from Nitinol, titanium, stainless steel, plastics, or absorbable PDS or PGA (poly glycolic acid). As for the diameter of the anchor, it should be shaped and dimensioned with a diameter sufficient to pass through the tissue to which it is secured without adversely affecting the tissue.

In accordance with a preferred embodiment, the proximal end of the applicator body 24 includes a barbed attachment member 44 shaped and dimensioned for attachment to the distal end of a shaft 46 coupling the applicator body 24 to the handle 48 of the gastric reduction apparatus 10 located at the proximal end of the apparatus 10. The attachment member 44 brings the applicator body 24 into communication with the suction line of the shaft 46 for creation of a vacuum within the anterior and posterior suction slots 30, 32.

As discussed above, the anterior and posterior suction slots 30, 32 are shaped and dimensioned for allowing stomach tissue to be sucked therein such that the tissue comes into intimate contact with the applicator body 24 for penetration of the corkscrew anchor 12 as the corkscrew anchor 12 is rotated.

Tissue retention bars 18, 20 are also provided for tracking the corkscrew anchor 12. It is also contemplated the retention bars 18, 20 may be used for securely holding tissue within the anterior and posterior suction slots 30, 32 during application of the corkscrew anchors 12. In particular, first and second tissue retention bars 18, 20 are positioned on opposite sides of each of the respective anterior and posterior suction slot 30, 32. The retention bars 18, 20 move longitudinally within the suction slots 30, 32 to allow for engagement with tissue suctioned within the suction slots 30, 32. The tissue retention bars 18, 20 are controlled via cables (not shown) extending between the applicator body 24 and the handle 48 at the proximal end of the gastric reduction apparatus 10.

As briefly mentioned above, the gastric reduction apparatus 10 further includes a handle 48 on its proximal end. The handle 48 is generally opposite the applicator body 24 positioned at the distal end of the apparatus 10. The two ends are connected by the shaft 46, through which runs a gear shaft 50 for firing of the corkscrew anchor 12, a suction line 51 for the creation of a vacuum with the suctions slots 30, 32, and cables for controlling the first and second retention bars 18, 20.

The gear shaft 50 of the firing mechanism is coupled to the applicator body 24 for rotation of the corkscrew anchors 12 in a manner that will be discussed below in greater detail. With this in mind, the gear shaft 50 includes a proximal end connected to a knob 52 on the handle 48 for manual rotation of the gear shaft 50. The gear shaft 50 also includes a distal end connected to firing gears 54 (via a central gear 56) housed within the applicator body 24 for controlled rotation of the corkscrew anchor 12 during installation. In accordance with a preferred embodiment of the present invention, the central gear 56 drives the series of firing (or planetary) gears 54.

In practice, the gastric reduction apparatus 10 is introduced orally until the distal end of the apparatus 10, that is, the applicator body 24 reaches the stomach. The gastric reduction apparatus 10 is positioned at the desired location within the stomach for application of the corkscrew anchors 12 into both the posterior or anterior walls 14, 16.

Once the applicator body 24 of the gastric reduction apparatus 10 is properly positioned within the stomach (see FIG. 6), suction is drawn within the anterior and posterior suction slots 30, 32, and onto the posterior and anterior walls 14, 16 of the stomach, until the stomach tissue is drawn into the suction slots 30, 32 (see FIG. 7).

The corkscrew anchors 12 are then rotated and advanced longitudinally within the anterior and posterior suction slots 30, 32. The first and second retention bars 18, 20 prevent the corkscrew anchors 12 from riding up out of the suction slots 30, 32 (see FIG. 8).

Firing of the corkscrew anchors 12 is achieved by rotation of the corkscrew firing gears 54 that are releasably coupled to corkscrew anchors 12. The corkscrew firing gears 54 are caused to rotate by the rotation of the central gear 56 that is driven by the gear shaft 50. The gear shaft 50 is ultimately connected to the knob 52 in the handle 48 such that the medical practitioner performing the procedure may control rotation of the corkscrew anchors 12 and ultimately the installation of the corkscrew anchors 12.

After the corkscrew anchors 12 are fired, the first and second retention bars 18, 20 are retracted and light insufflation is applied. The corkscrew anchors 12 at this point have spiraled through the pre-woven suture 22 held in place by retaining members 23 and the suture 22 may then be utilized to cinch the corkscrew anchors 12 together to form the gastric restriction (see FIG. 9). The suture is fastened with releasable tape or slots. The tips of the respective corkscrew anchors 12, on spiraling forward, advance through segments of the suture path such that the suture 22 and the corkscrew anchors 12 on each side of the device 10 are operatively coupled on extraction of the device (see FIGS. 1, 4, 6, 7, 8 and 9). The suture 22 is then cinched, drawing the anterior and posterior walls 14, 16 of the stomach into apposition. A suture clip is placed on a proximal end of the suture to retain the apposition of the anterior and posterior walls. Alternatively, the suture can be tied to retain the apposition.

In addition, tissue glue may be used in conjunction with the anchor to improve the seal resulting therefrom. Fibrin based glues such as those available from Ethicon could be used to adhere the tissue together.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A gastric reduction apparatus for endoscopically drawing stomach walls into apposition, comprising:
   at least an anterior corkscrew anchor and a posterior corkscrew anchor;
   an applicator body including a proximal end and a distal end and longitudinally extending exterior side wall therebetween, the applicator body also includes an anterior suction slot defining an opening in the exterior side wall and a posterior suction slot defining an opening in the exterior side wall, the anterior suction slot and the posterior suction slot being diametrically opposed along the exterior side wall of the applicator body which are shaped and dimensioned for housing the respective anterior corkscrew anchor and posterior corkscrew anchor and a suction line for the creation of a vacuum in the respective anterior suction slot and posterior suction slot; and
   a firing mechanism associated with the anterior corkscrew anchor and posterior corkscrew anchor for rotation of the corkscrew anchors in a manner causing the anterior corkscrew anchor and the posterior corkscrew anchor to penetrate and engage tissue brought adjacent the respective anterior suction slot and the posterior suction slot.

2. The gastric reduction apparatus according to claim 1, wherein each of the anterior suction slot and posterior suction slot includes at least one retention bar for assisting in guiding the respective anterior corkscrew anchor and posterior corkscrew anchor within the anterior suction slot and the posterior suction slot.

3. The gastric reduction apparatus according to claim 1, wherein the firing mechanism is a gear assembly.

4. The gastric reduction apparatus according to claim 3, wherein the gear assembly includes a gear shaft and firing gears.

5. The gastric reduction apparatus according to claim 1, furthering including a pre-woven suture linked to the anterior corkscrew anchor and the posterior corkscrew anchor.

* * * * *